United States Patent [19]
Christensen et al.

[11] Patent Number: 4,571,424
[45] Date of Patent: Feb. 18, 1986

[54] OPTICAL RESOLUTION OF RACEMIC FEMOXETINE

[75] Inventors: Jorgen A. Christensen, Virum; Peer Everland, Bagsvaerd, both of Denmark

[73] Assignee: A/S Ferrosan, Soborg, Denmark

[21] Appl. No.: 584,721

[22] Filed: Feb. 29, 1984

[30] Foreign Application Priority Data

Mar. 7, 1983 [DK] Denmark ............................. 1115/83

[51] Int. Cl.$^4$ .......................................... C07D 211/22
[52] U.S. Cl. ................................................... 546/236
[58] Field of Search ........................................ 546/236

[56] References Cited

FOREIGN PATENT DOCUMENTS 1422263  1/1976  United Kingdom ................ 546/236

OTHER PUBLICATIONS

J. C. Craig et al., Jour. Org. Chem., vol. 36 (23) (1971), pp. 3648–3649.

*Primary Examiner*—Norma S. Milestone
*Attorney, Agent, or Firm*—Gordon W. Hueschen

[57] ABSTRACT

A process for the optical resolution of the enantiomers of trans-3-[(4-methoxyphenoxy)-methyl]-1-methyl-4-phenylpiperidine, which involves reaction with an enantiomer of mandelic acid to form a mixture of diastereomeric compounds, precipitating one of the diastereoisomers, and converting it to the desirable free (+)-trans isomer, as well as the key diastereomeric isomer intermediate, is disclosed.

10 Claims, No Drawings

OPTICAL RESOLUTION OF RACEMIC FEMOXETINE

The present invention relates to a new process for the optical resolution of racemic trans-3-[(4-methoxyphenoxy)-methyl]-1-methyl-4-phenylpiperidine into its optical pure forms, of which the (+)-enantiomer is the antidepressive drug femoxetine having the structural formula

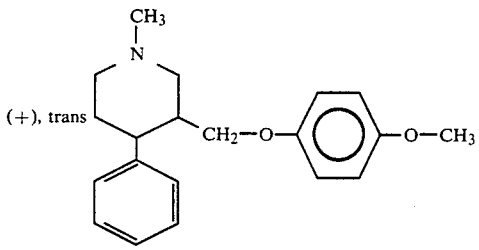

A conventional procedure for the optical resolution of a racemate into its optical active components comprises reacting the racemate with an optical compound to form two diastereomeric compounds, which because of their different physical properties can be separated by fractionated crystallization from a solvent, in which the solubility of the two compounds is different.

The preliminary step of the procedure for the optical resolution of a racemic compound by employing an optical active resolving agent usually comprises a step of mixing equimolar amounts of the racemate and the resolving agent each dissolved in a suitable solvent or mixing a hot solution of the racemate with an equimolar amount of the resolving agent. Following dissolution of the reactants the solution is allowed to cool to a temperature at which only one of the diastereomers precipitates. The optical active component of the racemate to be resolved is then recovered from the precipitated diastereomer by well known procedures.

British patent specification No. 1 422 263 discloses a process for the optical resolution of various racemates of 3-substituted-4-phenylipiperidine compounds including trans-3-[(4-methoxyphenoxy)-methyl]-1-methyl-4-phenylpiperidine using (−)-dibenzoyltartaric acid as the resolving agent. The process is exemplified by the optical resolution of racemic trans-3-methoxymethyl-1-methyl-4-phenylpiperidine.

However, the optical resolution of a mixture of the enantiometers of trans-3-[(4-methoxyphenoxy)-methyl]-1-methyl-4-phenylpiperidine using (−)-dibenzoyltartaric acid as the resolving agent suffers from the defects that the yield obtained is only about 47% of the theoretical value, that the precipitated (+)-trans-3-[(4-methoxyphenoxy)-methyl]-1-methyl-4-phenylpiperidine, (−)-dibenzoyltartrate is impure, and that (−)-dibenzoyltartaric acid is relatively costly. The high cost of the (−)-dibenzoyltartaric acid makes it desirable to recover it from the precipitated diastereomeric compound, but this has turned out to be difficult. Therefore the prior art process is of little value for commercial production of femoxetine.

Surprisingly it has now been found that an improved optical resolution of a mixture of the enantiomers of trans-3-[(4-methoxyphenoxy)-methyl]-1-methyl-4-phenylpiperidine can be effected by use of less than equimolar amounts of one of the enantiomers of mandelic acid or of a derivative thereof as the resolving agent in an organic solvent.

Accordingly, the present invention provides an improved process for the production of (+)-trans-3-((4-methoxyphenoxy)-methyl)-1-methyl-4-phenylpiperidine from racemic trans-3-((4-methoxyphenoxy)-methyl)-1-methyl-4-phenylpiperidine, which comprises reacting said racemic trans-3-((4-methoxyphenoxy)-methyl)-1-methyl-4-phenylpiperidine with one of the enantiomers of mandelic acid or of a derivative thereof in less than stoichiometric amounts in an organic solvent to form two diastereomeric compounds in mixture with excess trans-3-((4-methoxyphenoxy)-methyl)-1-methyl-4-phenylpiperidine, and which process comprises, from this mixture, precipitating one of said diastereomeric compounds in high yield of the theoretical possible amount.

It is evident that the present invention provides an exceptional example to separation of optical isomers by fractional crystallization as difference in solubilities of diastereomers rarely if ever is great enough to effect total separation with one crystallization (see J. March., Advanced Organic Chemistry, McGraw-Hill, Inc. (1977)).

In a preferred embodiment of the process according to the present invention said enantiomer of mandelic acid or a derivative thereof is reacted with a mixture of the enantiomers of trans-3-[(4-methoxyphenoxy)-methyl]-1-methyl-4-phenylpiperidine dissolved in a hot organic solvent.

In a preferred embodiment of the present invention one of said diastereomeric compounds is precipitated by cooling the solution to a temperature at which only said diastereomeric compound precipitates.

The organic solvent used as reaction medium is preferably an aromatic solvent including for example alkylated and halogenated derivatives, an aliphatic ester, an aliphatic alcohol or a mixture thereof. The organic solvent is most preferably toluene, ethyl acetate, methyl isobutyl carbinol or mixtures thereof.

The resolving agent is preferably (+)-mandelic acid or a derivative thereof, most preferably (+)-mandelic acid.

Derivatives of (+)-mandelic acid include derivatives which are halogenated, hydroxylated, nitrated, alkylated or alkoxylated. Most preferred derivatives are those which are halogenated. Most preferred halogenated derivatives are those which are halogenated in 4 position of the phenyl group.

When using (+)-mandelic acid as the resolving agent and toluene as the solvent the precipitation is preferably carried out by cooling the solution to a temperature between 0° and 30° C.

The mixture of the enantiomers of trans-3-[(4-methoxyphenoxy)-methyl]-1-methyl-4-phenylpiperidine is preferably dissolved in 0.3 to 0.4 l of toluene for each mol of trans-3-[(4-methoxyphenoxy)-methyl]-1-methyl-4-phenylpiperidine, and the toluene is preferably heated to a temperature between 50° and 75° C.

The amount of (+)-mandelic acid is preferably from 0.5 to 0.6 mol for each mol of trans-3-[(4-methoxyphenoxy)-methyl]-1-methyl-4-phenylpiperidine. Despite the small amount of the resolving agent used the yield of (+)-trans-3-[(4-methoxyphenoxy)-methyl]-1-methyl-4-phenylpiperidine, (+)-mandelate is approximately 75% of the theoretical value and said mandelate is of a very high purity.

Not only does said preferred embodiment of the process require less than equimolar amounts of the (+)-mandelic acid, but it has also been found that the (+)-mandelic acid as well as racemic trans-3-[(4-methoxyphenoxy)-methyl]-1-methyl-4-phenylpiperidine left in the solution can easily be recovered and recycled, thus only leaving the (−)-trans-3-[(4-methoxyphenoxy)-methyl]-1-methyl-4-phenylpiperidine as waste product. The following examples illustrate the invention.

EXAMPLE 1

116.4 kg (383.7 mol) of racemic trans-3-[(4-methoxyphenoxy)-methyl]-1-methyl-4-phenylpiperidine was dissolved in 100 l of toluene. The solution was stirred while the temperature was raised to 60° C. 31.2 kg (205.5 mol) of (+)-mandelic acid was added and the mixture was stirred at 60° C. until the mixture was clear. The solution was allowed to cool to room temperature. The temperature of the mixture was then reduced to 10° C. while stirring during the next 15 hours. The mixture was then centrifuged and the precipitate was washed with toluene and iso-propanol. The yield was 64.8 kg (75% of the theoretical value) of (+)-trans-3-[(4-methoxyphenoxy)-methyl]-1-methyl-4-phenylpiperidine, (+)-mandelate, m.p. 126°-30° C., $[\alpha]_D^{20}+90.2°$ (C=2 in 96% ethanol). Recrystallization of said mandelate salt did not change the value of $[\alpha]_D^{20}$.

50 kg of (+)-trans-3-[(4-methoxyphenoxy)-methyl]-1-methyl-4-phenylpiperidine, (+)-mandelate was mixed with 27.5 l of distilled water, 67.5 l of toluene and 6.1 l of 50% w/w NaOH. The toluene phase was separated and stirred with 3.3 kg of potassium carbonate and filtered. 10 l of concentrated hydrochloric acid and 45 l of isopropanol was mixed with the toluene phase and the mixture was evaporated. The residue was recrystallized from iso-propanol to give 33.8 kg (90%) of (+)-trans-3-[(4-methoxyphenoxy)-methyl]-1-methyl-4-phenylpiperidine as the hydrochloride. M.p. 189°-90° C., $[\alpha]_D^{20}=75.3°$ (C=5 in H$_2$O).

EXAMPLES 2-5

In a similar manner but by use of different solvents and different mandelic acid derivatives in an amount counting for 55% of the racemic trans-3-[(4-methoxyphenoxy)-methyl]-1-methyl-4-phenylpiperidine the experiment was repeated. The table below shows the overall yield of the salt of (+)-trans-3-[(4-methoxyphenoxy)-methyl]-1-methyl-4-phenylpiperidine (femoxetine) and (+)-mandelic acid or a derivative thereof.

| Ex. | Solvent | Resolving agent | Overall yield of the salt of femoxetine and (+)-mandelic acid or a derivative thereof (%) |
|---|---|---|---|
|  | toluene | (+)-2-hydroxy-2-(4-fluoro-phenyl)-acetic acid | 74.0 |
| 3 | toluene | (+)-2-hydroxy-2-(4-chloro-phenyl)-acetic acid | 66.5 |
| 4 | ethyl acetate | (+)-2-hydroxy-2-phenyl-acetic acid | 67.5 |
| 5 | MIBC* | (+)-2-hydroxy-2-phenyl-acetic acid | 59.0 |

*MIBC = methyl iso-butyl carbinol

The results thus obtained clearly show that the present invention provides an improved process for the production of femoxetine in that the yield of the salt of femoxetine and (+)-mandelic acid or a derivative thereof is 65-75% of the theoretical value compared to 47% obtained by the known methods. Furthermore said salt of femoxetine and (+)-mandelic acid or a derivative thereof is of very high purity.

EXAMPLE 6

15.0 g (48.2 mmol) of racemic trans-3((4-methoxyphenoxy)-methyl)-1-methyl-4-phenylpiperidine was dissolved in 11.5 ml of toluene. The solution was stirred while the temperature was raised to 60° C. 6.55 g (43.1 mmol) of (+)-mandelic acid was added and the mixture was stirred at 60° C. until the mixture was clear. The solution was allowed to cool to room temperature. The temperature of the mixture was then reduced to 10° C. and the mixture was left at this temperature for the next 15 hours. The mixture was then filtered and the precipitate was washed with toluene and iso-propanol. The yield was 6.1 g (55% of the theoretical value) of (+)-trans-3-((4-methoxyphenoxy)-methyl)-1-methyl-4-phenylpiperidine, (+)-mandelate, m.p. 121° C., $\alpha_D^{20}+81.6°$ (C=2 in 96% ethanol).

EXAMPLE 7

(a) 20 g (64 mmol) of racemic trans-3-[(4-methoxyphenoxy)-methyl]-1-methyl-4-phenylpiperidine and 22 g (62 mmol) of (−)-dibenzoyl tartaric acid is dissolved in 200 ml of ethanol. The mixture is evaporated under vacuum. The residue is optimally recrystallized from 50 ml methanol to yield 16.2 g of product. M.p. 84.1°-84.6° C. $[\alpha]_D^{20}$ 0.38 (c=5 in 99% ethanol).

(b) 100 g of the product of a is mixed with 20 ml of 4M NaOH, 40 ml of water and 100 ml of ether. The organic phase is dried with potassium carbonate, filtered and evaporated under vacuum to give 4.2 g of product. The product is dissolved in 75 ml of iso-propanol. 1 ml of conc. hydrochloric acid is added and the mixture is evaporated to give 4.7 g of product. M.p. 182.7°-184.2° C. 1.9 g of this product is recrystallized from 6 ml of iso-propanol to give 1.4 of (+)-trans-3-[(4-methoxyphenoxy)-methyl]-1-methyl-4-phenylpiperidine as the hydrochloride. M.p. 189.4° C. $\alpha_D^{20}$ 75.6° (c=5 in H$_2$O). Overall yield of the hydrochloride is 47% of theoretical amount.

EXAMPLE 8

The toluene solution of example 1 from which (+)-trans-3-[(4-methoxyphenoxy)-methyl-]-1-methyl-4-phenylpiperidine (+)-mandelate is precipitated is mixed with 13 l of 9 M aqueous NaOH and 14 l of water. The mixture is stirred and this aqueous phase is mixed with the aqueous phase of example 1 and heated to 40° C. To this mixture is added 23 l of conc. hydrochloric acid ensuring that pH is around 1.5. The mixture is cooled and stirred. When the temperature is around 10° C. the precipitate is separated and washed 1 time with 10 l of water giving 26.5 kg of (+)-mandelic acid. M.p. 130°-3° C. Yield of theoretical amount is 85%.

We claim:

1. A process for the optical resolution of a mixture of the (+) and (−) enantiomers of trans-3-[(4-methoxyphenoxy)-methyl]-1-methyl-4-phenylpiperidine, characterized in reacting said mixture of the (+) and (−) enantiomers of trans-3-[(4-methoxyphenoxy)-methyl]-1-methyl-4-phenylpiperidine with less than the stoichiometric amount of the (+) enantiomer of mandelic acid or a 4-halo derivative thereof in an organic solvent from which the (+) (+) enantiomer precipitates to form two diastereomeric compounds, precipitating the (+) (+) diastereomeric compound from said solvent, and converting said precipitated compound into the free (+)-trans-3-[(4-methoxyphenoxy)-methyl]-1-methyl-4-phenylpiperidine or a pharmaceutically-acceptable salt thereof.

2. A process according to claim 1 characterized in that (±)-trans-3-[(4-methoxyphenoxy)-methyl]-1-methyl-4-phenylpiperidine is reacted with 0.5 to 0.6 mol of (+)-mandelic acid or a 4-halo derivative thereof for each mol of the racemic compound.

3. A process according to claim 1 characterized in that a 4-halo derivative of (+)-mandelic acid is employed.

4. A process according to claim 1, characterized in that (±)-trans-3-[(4-methoxyphenoxy)-methyl]-1-methyl-4-phenylpiperidine is reacted with (+)-mandelic acid or a 4-halo derivative thereof in a hot organic solvent.

5. A process according to claim 4 characterized in that the formed diastereomeric compound is precipitated by cooling the solution to a temperature at which only the diastereomeric compound containing (+)-trans-[(4-methoxyphenoxy)-methyl]-1-methyl-4-phenylpiperidine precipitates.

6. A process according to claim 4 characterized in that the organic solvent is an aromatic solvent, an aliphatic ester, an aliphatic alcohol or a mixture thereof.

7. A process according to claim 4, 5, or 6, characterized in that (±)-trans-3-[(4-methoxyphenoxy)-methyl]-1-methyl-4-phenylpiperidine dissolved in hot toluene is reacted with (+)-mandelic acid and that the precipitation is carried out by cooling the solution to a temperature between 0° and 30° C.

8. A process according to claim 4, 5, or 6, characterized that (±)-trans-3-[(4-methoxyphenoxy)-methyl]-1-methyl-4-phenylpiperidine is dissolved in 0.3 to 0.4 l of toluene for each mole of the racemic compound, and that the toluene is heated to a temperature between 50° and 75° C.

9. A process according to claim 1 or 2 characterized in that (+)-mandelic acid or a 4-halo derivative thereof is recovered from mother liqueurs of the resolution process by extraction into basic water, acidification and precipitation therefrom.

10. (+)-trans-3-[(4-methoxyphenoxy)-methyl]-1-methyl-4-phenylpiperidine (+)-mandelate.

* * * * *

UNITED STATES PATENT AND TRADEMARK OFFICE
CERTIFICATE OF CORRECTION

PATENT NO. : 4,571,424

DATED : February 18, 1986

INVENTOR(S) : Jørgen A. Christensen and Peer Everland

It is certified that error appears in the above-identified patent and that said Letters Patent is hereby corrected as shown below:

Col. 1, line 44; "-phenylipiperidine" should read -- -phenylpiperidine --

Col. 1, line 51; "enantiometers" should read -- enantiomers --

Col. 1, line 57; "dibenzyltartrate" (first word of the line) should read -- dibenzoyltartrate --

Col. 3, approximately line 58 (in the table, first column under "Ex."; the first "Ex." is blank, but it should read -- 2 --

Signed and Sealed this

Twenty-second Day of July 1986

[SEAL]

Attest:

DONALD J. QUIGG

Attesting Officer

Commissioner of Patents and Trademarks